US010161913B2

(12) United States Patent
Cendras et al.

(10) Patent No.: US 10,161,913 B2
(45) Date of Patent: Dec. 25, 2018

(54) METAL WELD INSPECTION DEVICE, ASSOCIATED SYSTEM AND METHOD

(71) Applicants: THALES, Courbevoie (FR); SONAXIS, Besancon (FR)

(72) Inventors: Michel Cendras, Cannes la Bocca (FR); Guillaume Pierre, Besancon (FR); Sophie Crozat, Besancon (FR); Stéphane Bey, Besancon (FR)

(73) Assignees: THALES, Courbevoie (FR); SONAXIS, Besancon (FR)

( * ) Notice: Subject to any disclaimer, the term of this patent is extended or adjusted under 35 U.S.C. 154(b) by 110 days.

(21) Appl. No.: 14/916,960

(22) PCT Filed: Sep. 9, 2014

(86) PCT No.: PCT/EP2014/069227
§ 371 (c)(1),
(2) Date: Mar. 4, 2016

(87) PCT Pub. No.: WO2015/036407
PCT Pub. Date: Mar. 19, 2015

(65) Prior Publication Data
US 2016/0209374 A1 Jul. 21, 2016

(30) Foreign Application Priority Data

Sep. 10, 2013 (FR) .................................... 13 02107

(51) Int. Cl.
*G01N 29/22* (2006.01)
*G01N 29/04* (2006.01)
*G01N 29/265* (2006.01)

(52) U.S. Cl.
CPC ........... *G01N 29/226* (2013.01); *G01N 29/04* (2013.01); *G01N 29/043* (2013.01);
(Continued)

(58) Field of Classification Search
CPC .... G01N 29/226; G01N 29/04; G01N 29/043; G01N 29/265; G01N 29/223; G01N 29/225; G01N 29/28
See application file for complete search history.

(56) References Cited

U.S. PATENT DOCUMENTS 4,331,034 A * 5/1982 Takeda ................. G01N 29/265
376/252
4,843,884 A * 7/1989 House .................... G01N 29/26
73/622

(Continued)

FOREIGN PATENT DOCUMENTS

CA      2 545 285 A1    5/2005
JP      2011-058980 A   3/2011
WO   WO 2005/048271    *  5/2005

*Primary Examiner* — Helen Kwok
(74) *Attorney, Agent, or Firm* — Baker & Hostetler LLP

(57) ABSTRACT

A portable device for inspecting a weld of metal tubes, comprises: at least one clamp formed from two jaws, each jaw including a circularly arcuate void defining, once the clamp has been closed, a substantially circular slot suitable for receiving a tube the weld of which is to be inspected; at least two multielement ultrasound probes that are mounted to be movable relative to the inspecting device and to be able to rotate relative to an axis passing through the center of the two lateral portions of the substantially circular slot of a clamp; a means configured to drive the ultrasound probes to rotate to pass around the entire circumference of the weld to be inspected; and an angular sensor configured to deliver a signal representative of the angular position of at least one sensor relative to an initial position.

9 Claims, 3 Drawing Sheets

(52) U.S. Cl.
CPC ... *G01N 29/265* (2013.01); *G01N 2291/0234* (2013.01); *G01N 2291/0289* (2013.01); *G01N 2291/044* (2013.01); *G01N 2291/106* (2013.01); *G01N 2291/2634* (2013.01); *G01N 2291/2675* (2013.01)

(56) References Cited

U.S. PATENT DOCUMENTS

| | | | | |
|---|---|---|---|---|
| 6,222,897 B1 * | 4/2001 | Hatley | ................ | G01N 29/223 376/245 |
| 6,497,159 B1 * | 12/2002 | Lavoie | ................ | G01B 17/02 73/661 |
| 6,536,283 B1 * | 3/2003 | Hatley | ................ | G21C 17/017 376/249 |
| 7,240,556 B2 * | 7/2007 | Georgeson | ........... | G01N 29/041 73/620 |
| 7,624,651 B2 * | 12/2009 | Fernald | ................ | G01F 1/7082 73/861.27 |
| 7,950,298 B2 * | 5/2011 | Lavoie | ................ | G01N 29/225 73/866.5 |
| 7,963,175 B2 * | 6/2011 | Gysling | ................ | G01F 1/662 73/861.27 |
| 7,997,139 B2 * | 8/2011 | Owens | ............... | G01N 29/2412 702/39 |
| 8,146,430 B2 * | 4/2012 | Simmons | ............... | G01N 29/04 73/592 |
| 8,365,601 B2 * | 2/2013 | Minachi | ................ | G01B 17/02 73/602 |
| 8,590,383 B2 * | 11/2013 | Brignac | ............... | G01N 29/226 376/252 |
| 2004/0020298 A1 * | 2/2004 | Siverling | ............. | G01N 29/275 73/644 |
| 2009/0025490 A1 * | 1/2009 | Brandstrom | ......... | G01B 21/047 73/865.9 |

* cited by examiner

METAL WELD INSPECTION DEVICE, ASSOCIATED SYSTEM AND METHOD

CROSS-REFERENCE TO RELATED APPLICATIONS

This application is a National Stage of International patent application PCT/EP2014/069227, filed on Sep. 9, 2014, which claims priority to foreign French patent application No. FR 1302107, filed on Sep. 10, 2013, the disclosures of which are incorporated by reference in their entirety.

FIELD OF THE INVENTION

The present invention relates to the field of nondestructive inspection of metal welds. The present invention more particularly relates to a device for inspecting a metal weld, and to an associated system and method.

BACKGROUND

Welding is commonly used to join many metal elements such as for example metal tubes. The metal welding may lead to various types of defects such as, for example, problems with cracking, inadequate penetration, inadequate coverage, problems with blow holing, oxidation or gaseous inclusions (blistering). In certain fields of application, such as for example and nonlimitingly the aerospace or aeronautic field, the quality and reliability of the weld must be guaranteed to be of the highest possible standard. In this context, it is advantageous to have at one's disposal a solution allowing the integrity of the welds produced on a metal tube to be inspected.

Conventionally, welds are inspected by X- or γ-ray radiology; however, this method has many drawbacks. A first drawback is the inspecting equipment. Specifically, these systems are heavy and bulky. During the radiography, very severe constraints are imposed by radiation protection: the item to be inspected must be transferred to a dedicated booth or personnel must be evacuated from a zone of consequent size. Once the radiography has been carried out, it is necessary to wait for the radio films to be developed before the inspection results can be interpreted. Regarding the interpretation of the results, locating defects on the periphery of the tubes is difficult. In addition, the detection of critical defects is dependent on the orientation of said defect.

Devices using an ultrasound inspecting method to verify the integrity of welds produced on tubes of large size, for example in the oil and gas field, do exist, but these devices are not easily transposable to the aeronautic industry.

SUMMARY OF THE INVENTION

One aim of the invention is especially to correct at least certain drawbacks of the prior art, especially by providing a portable device and a system for inspecting a metal weld and a method allowing any defects inside a metal weld to be detected, quantified and located so as to make it possible to judge the conformity of the latter.

To this end, one subject of the invention is a portable device for inspecting a weld of small-diameter metal tubes, comprising:

at least one clamp formed from two jaws, each jaw including a circularly arcuate void defining, once the clamp has been closed, a substantially circular slot suitable for receiving a tube the weld of which is to be inspected;

at least two multielement ultrasound probes that are mounted so as to be movable relative to said inspecting device and that are mounted so as to be able to rotate relative to an axis passing through the center of the two lateral portions of the substantially circular slot of a clamp, said probes being configured to deliver as output electrical signals proportional to the echoes received by said probes;

a means configured to drive the ultrasound probes to rotate so as to pass around the entire circumference of the weld to be inspected; and an angular sensor configured to deliver as output a signal representative of the angular position of at least one sensor relative to an initial position.

According to one embodiment, the elements of the probe are configured to emit ultrasound beams that are oriented at an angle different from 90° to an axis passing through the center of the two lateral portions of the substantially circular slot of a clamp.

According to one embodiment, the elements of two ultrasound probes are aligned along two axes that are oriented so that said axes are not symmetric about an axis passing through the center of the two lateral portions of the substantially circular slot of a clamp.

According to one embodiment, each element of the ultrasound probes is individually controllable.

According to one embodiment, the means configured to drive the ultrasound probes to rotate is a manual means.

According to one embodiment, the means configured to drive the ultrasound probes to rotate is a motorized means.

Another subject of the invention is a system for inspecting a weld of metal tubes, comprising a device for inspecting a weld of metal tubes such as described above, a processing unit and a viewing unit, said processing unit being configured to emit signals in the direction of each ultrasound probe of said weld inspecting device so as to control each element of said probes and to receive signals proportional to the echoes received by each element of said probes, the viewing unit being configured to represent, on said viewing unit, the signals received from the probes after processing in the form of images as a function of the angular position of at least one probe.

According to one embodiment, the processing unit is programmed to transmit, to each element of the probes, switching signals so as to sequentially power a group of adjacent elements in order to linearly scan the width of the weld bead to be inspected.

According to one embodiment, the processing unit is configured to transmit, to each element of the probes, control signals respecting a delay law so as to electronically deviate the ultrasound beam emitted by said probes.

According to one embodiment, the processing unit is configured to transmit, to each element of the probes, a signal proportional to the intensity of the ultrasound beam to be emitted by said probes.

Another subject of the invention is a method for inspecting a weld of metal tubes employing the weld inspecting system described above, comprising:

a step of coating probes with coupling gel;

a step of positioning the inspecting device on the tube, level with the weld to be inspected so as to align the probes with said weld;

a step of acquiring, to a memory zone of the processing unit, the signal representative of the initial angular position of at least one probe;

a step of rotating the probes around the weld to be inspected and, at regular intervals, simultaneously measuring and recording, to a memory zone of the processing unit, the signal representative of the angular position of at least one probe and the signal representative of the echoes captured by the elements of the probes; and a step of displaying, on the viewing unit, images representative of the signals received by the elements of the probes as a function of the angular position of the latter.

Other particularities and advantages of the present invention will become more clearly apparent on reading the following nonlimiting illustrative description given with reference to the appended drawings, in which:

BRIEF DESCRIPTION OF THE DRAWING

Other particularities and advantages of the present invention will become more clearly apparent on reading the following nonlimiting illustrative description given with reference to the appended drawings, in which.

DETAILED DESCRIPTION

It should be noted that, below, the expressions "ultrasound transducer" or "ultrasound probe element" designate any element that converts an ultrasonic wave into an electrical signal and vice versa.

The present invention relates to the inspection of a metal weld by ultrasound. The device and system according to the invention are suitable for inspecting welds produced on metal tubes of small diameter, commonly used for example in the aeronautic or astronautic fields. By "small-diameter tube" or "tube of small diameter" what is meant is tubes of diameter smaller than one inch i.e. about 25.4 millimeters.

In these fields, commonly used metals are, for example and nonlimitingly, titanium, stainless steel and special steels. Likewise commonly used welding techniques are for example TIG (tungsten inert gas) welding and electron-beam or friction welding.

Figure 1:
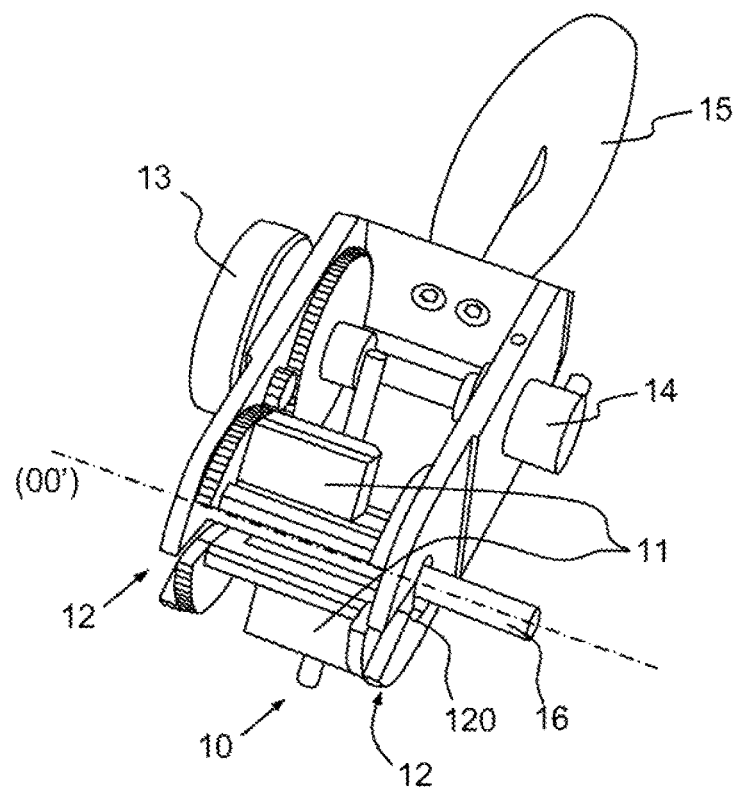
FIG. 1 shows a preferred exemplary embodiment of an inspecting device according to the invention.
Figure 2:
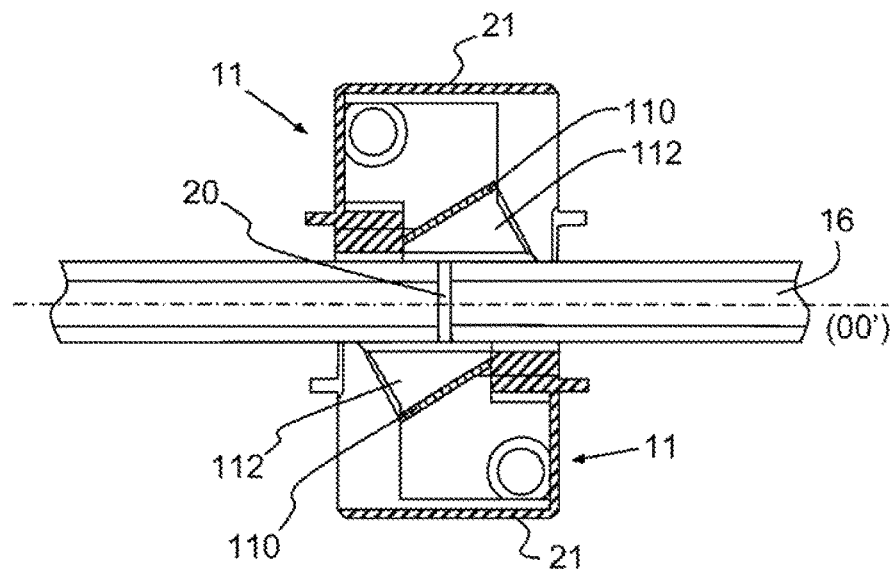
FIG. 2 shows an exemplary embodiment of ultrasound probes.

FIG. 1 shows a preferred exemplary embodiment of a portable device 10 for inspecting a weld 20 of a metal tube 16 of small diameter, according to the invention.

According to one embodiment, the device 10 comprises at least two multielement ultrasound probes 11, at least one clamp 12, a means 13 configured to drive the ultrasound probes 11 to rotate around the periphery of the weld bead 20 to be inspected and an angular sensor 14.

According to one embodiment, the portable device 10 may comprise a holding handle 15.

The clamp 12 of the device 10 may be formed from two jaws intended to clasp the tube 16 the weld of which is to be inspected so as to hold said inspecting device 10 on said tube 16.

Each of these jaws of the clamp 12 may possess a circularly arcuate void defining, once the clamp 12 has been closed, a substantially circular slot 120 suitable for receiving a tube 16 the weld bead 20 of which is to be inspected.

According to one exemplary embodiment, the clamp 12 of the device 10 is formed by the group comprising at least two multielement probes 11 in order to form jaws intended to clasp a tube 16 the weld of which is to be inspected.

Each element 110 of the probes 11 may possess a circularly arcuate base so as to closely follow the shape of the tube 16 the weld of which is to be checked. Thus, the clamp, once closed, defines a substantially circular slot 120 suitable for receiving a tube 16 the weld bead 20 of which is to be inspected.

According to one embodiment, the probes 11 may be held pressed against the tube 16 the weld bead of which is to be checked by a return spring.

Figure 4:
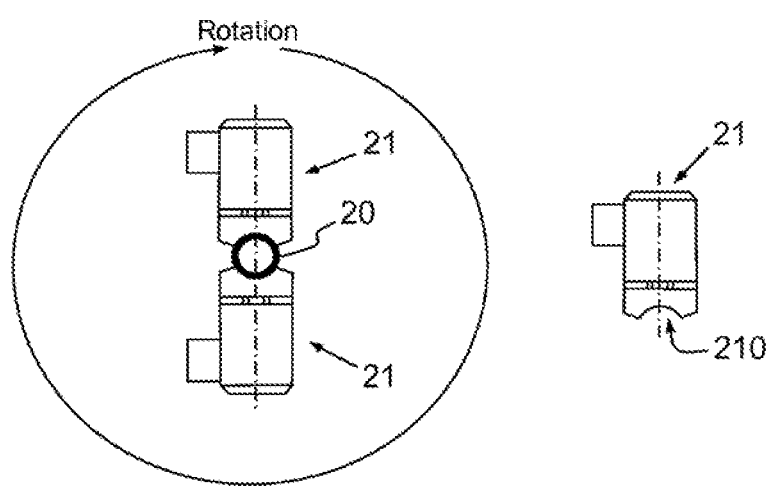
FIG. 4 shows wedge views of ultrasound probes.

The ultrasound probes 11 are mounted so as to be movable relative to the inspecting device 10 and to be rotatable relative to an axis (O, O') passing through the center of the two lateral portions of the substantially circular slot 120 of the clamps 12. This rotatability allows the ultrasound probes 12 to pass around the entire periphery of the weld bead 20 to be inspected, without having to move the inspecting device 10. As illustrated in FIG. 4, each probe 11 may make a complete turn around the weld bead 20.

The probes 11 may be mounted in a holder also referred to as a wedge 21. In order to minimize the space between the probe and the tube the weld of which is to be checked, the wedge 21 may include a circularly arcuate void 210 as illustrated in FIG. 4.

Each element 110 of the probes may possess a circularly arcuate base so as to closely follow the shape of the wedge 21. As seen above, this allows the shape of the tube 16 the weld of which is to be checked to be closely followed. Advantageously, the circularly arcuate shape of the wedge 21 and/or elements 110 also allows the ultrasound beam to be focused so that it is directed along the axis of the tube 16 and not deviated toward the exterior. The circularly arcuate shape forms a lens and allows the beam to be made to converge on the axis of the tube.

The probes 11 are mutated by a means 13 configured to drive them to rotate. According to one exemplary embodiment illustrated in FIG. 1, this means 13 may be a manual means such as for example a rotatable knurling wheel. The knurling wheel may for example drive the probes 11 via a set of gears. According to another embodiment, the means 13 may be a motorized means such as for example a stepper motor.

The means 13 configured to drive the ultrasound probes 11 to rotate also drives an angular sensor 14 allowing the angular position of at least one probe relative to an initial position to be measured and an electrical signal proportional to the angular position of said probe 11 to be delivered. According to one exemplary embodiment, the means 13 configured to drive the ultrasound probes 11 and the angular sensor 14 to rotate are mounted on the same axis.

According to one embodiment, the manual rotating means 13 may possess a locking notch indicating the origin of the angular sensor 14, i.e. its initial position. This locking notch also allows the user to see when the probes 11 have made a complete turn around the weld 20 during the rotation of the latter.

The portable device 10 according to the invention is intended to be connected to at least one processing unit 50 and one viewing unit 51 in order to form a system for inspecting a weld of metal tubes.

The ultrasound probes 11 are "multielement" probes and are divided into a plurality of elementary piezoelectric ultrasound transducers or elements 110. Each element 110 of each probe 11 may be electronically controlled individually. This electronic control may be carried out by the processing unit 50.

According to one embodiment, the elements 110 of the probes 11 are arranged in a row in order to cover at least the width of the weld bead 20 to be inspected. Each element 110 of each probe may be electronically switched by the processing unit. To do this, the processing unit may comprise a control module 501 configured to transmit a switching signal to each element 110 of the ultrasound probe, in order to activate or inhibit one or more elements 110 of said probe 11. This switching allows the ultrasound beam 115 emitted by the probe 11 to be moved spatially by activating sequentially an element 110 or a group of adjacent elements 110. The probe 11 may thus carry out a linear electronic scan of the width of the weld bead 20. Advantageously, this linear electronic scan makes it possible to avoid moving the probe 11 or these elements 110 mechanically. Since an electronic scan is more rapid than a mechanical scan, this also makes it possible to acquire data at a higher speed.

According to one embodiment, each ultrasound element 110 is placed inclined in the wedge 21 of the probe 11 so that the angle made by the axis of the ultrasound beam 115 emitted by one or more elements 110 to the axis (O, O') passing through the center of the two lateral portions of the substantially circular slot 120 of a clamp 12 is different from a right angle. To this end, the elements 110 may, for example, be placed on a wedge 112.

Advantageously, this arrangement makes it possible to avoid problems with reflection of the ultrasound beam from the surface of the weld to be inspected.

The angle of inclination of the elements 110 in the wedge 21 of the probe 11 is also chosen so as to generate, in the material of the weld 20 to be inspected, a transverse wave.

Figure 3:
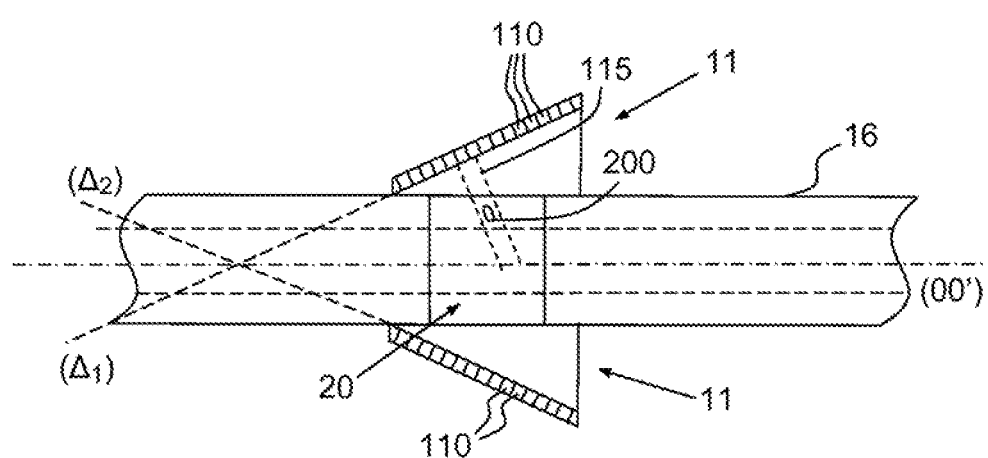
FIG. 3 shows an exemplary variant embodiment of the weld inspecting device.
Figure 6:
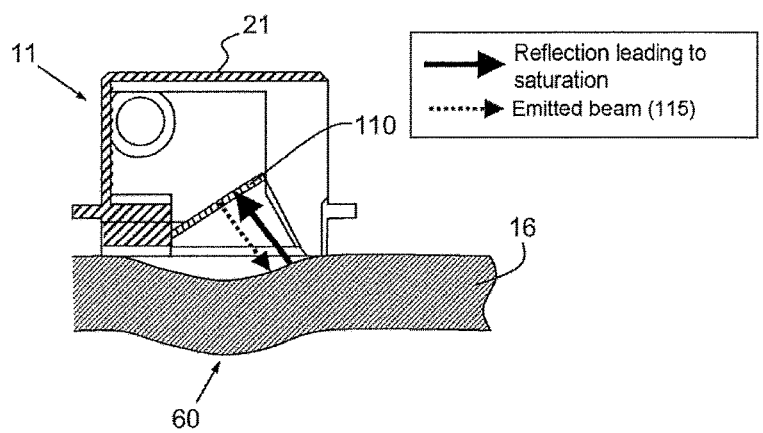
FIG. 6 shows a welding control example in presence of a defect in the weld bead.

Reference is now made to FIGS. 3 and 6. In this embodiment, the elements 110 of each ultrasound probe 11 are aligned along an axis $\Delta_1$, $\Delta_2$. Advantageously, the alignment axis $\Delta_1$ of the elements 110 of the first probe 11 and the alignment axis $\Delta_2$ of the elements 110 of the second probe 11 are chosen so that these two axes are not symmetric about an axis (O, O') passing through the center of the two lateral portions of the substantially circular slot (120) of a clamp (12).

Let us assume that these two alignment axes $\Delta_1$ and $\Delta_2$ are symmetric about an axis (O, O') passing through the center of the two lateral portions of the substantially circular slot (120) of a clamp (12) as illustrated in FIG. 3. Let us also assume that a defect 200 is present in the weld bead 20 to be analyzed and that this defect 200 is oriented in a direction parallel to the axis of the ultrasound beam 115 of one probe, this defect 200 would not be able to be detected by the probe 11. When the second probe 11 has made a half-turn, it will be oriented in the same way as the preceding probe when it occupies the same position and will therefore also not be able to detect the presence of the defect 200.

In contrast, if the two alignment axes $\Delta_1$ and $\Delta_2$ are not symmetric about the axis (O, O'), when the probes 11 make a half-turn the ultrasound beam 115 of the second probe 11 will not be oriented parallel to the axis of the defect 200, and the probe 11 may detect the presence and form of said defect 200.

The fact that the two alignment axes are not symmetric is also advantageous in the case of the presence of a sag 60 in the tube due to the welding. In the case of substantial sagging, the surface of the tube 16 may be oriented perpendicularly to the ultrasound beam 115 and cause a parasitic reflection leading to saturation of the probe 11. In this configuration, the probe 11 cannot analyze the weld bead. When the probes 11 have made a half-turn, the ultrasound beam 115 of the second probe 11 will not be oriented perpendicularly to the sag 60 and this probe 11 will be able to detect the presence and form of any defect 200.

The same problem may arise in the case of protrusions when welding tubes of slightly different thicknesses. This situation may for example arise when joining different pieces of equipment in the case where end fittings are present or in the case where the tubes welded have fairly lax manufacturing tolerances.

Advantageously, in order to simplify the processing calculations, the alignment axes $\Delta_1$ and $\Delta_2$ of the elements 110 of the probes 11 may be chosen to be substantially parallel.

In certain embodiments, the angle of the ultrasound beam 115 emitted by the probes 11 may be electronically modified. To this end, at the emission, the processing unit 50, for example via a control module 501, may transmit to each element 110 of the ultrasound probes 11, excitation signals respecting a delay law in order to obtain a phase shift between the elements 110. This allows a degree of freedom to be obtained in the angle of the ultrasound beam 115 by electronic management of the elements 110 of the probes 11. Since the angle of the ultrasound beam 115 in the interior of the weld depends on the acoustic impedance of the material used, this degree of freedom may advantageously allow welds produced on tubes of different materials to be inspected without having to modify the parameters of the processing program.

Analogously, delay laws may be applied on reception to the signals received by the various elements 110 of the probe before their summation.

Advantageously, this ability to electronically deflect the ultrasound beam may also make it possible, for example, to correct for any defects in the positioning of the elements 110 in the probe 11.

According to one embodiment, the processing unit 50 may be configured to transmit, for example via a control module 501, to each element 110 of the probes 11, an excitation signal proportional to the intensity of the ultrasound beam to be emitted.

In one preferred embodiment of the invention, the three aforementioned embodiments are combined. Thus, the processing unit of the system allows the angle of the ultrasound beam 115 to be varied electronically, the beam 115 to be scanned electronically and the intensity of said beam 115 to be varied.

Figure 5:
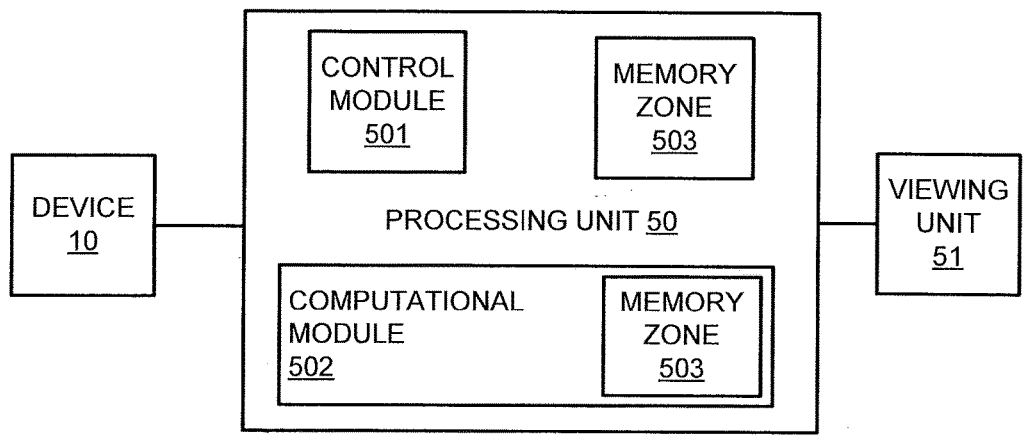
FIG. 5 shows an exemplary embodiment of the weld inspecting system according to the invention.

With reference to FIG. 5, the processing unit 50 is intended to manage the portable device 10 for inspecting a weld 20. As was seen above, the processing unit may manage the elements 110 of the ultrasound probes 11. To do this, it may comprise a control module 501 configured especially to switch elements 110 of the probe 11 and/or to manage the excitation signals of said elements 110.

This processing unit 50 also has the role of processing the signals issued from the ultrasound probes 11 of the device 10. To do this, the processing unit 50 may comprise a computational module 502 configured, for example, to acquire data originating from the control device 10, such as, for example, the signals output from the probes and/or angular sensor, and to process these data. To do this, the processing unit may comprise one or more memory zones 503. The processing of the data may, for example, be carried out by one or more programs stored in at least one memory zone 503 of the processing unit 50, such as, for example, a memory zone 503 of the computational module 502. The data processing used is conventional processing employed in the field of ultrasound imaging.

The processed data are then transmitted to a viewing unit 51 so as to display them on a display means in the form of images representative of the signals received by the elements 110 of the probes 11 as a function of the angular position of at least one probe 11.

Another subject of the invention is a method for inspecting a metal weld using the inspecting system described above.

The method comprises a first step of coating probes 11 with a coupling gel in order to facilitate the transmission of waves from the ultrasound elements 110 to the interior of the material of the weld bead 20 to be inspected. Once the probes have been coated, the inspecting device 10 is positioned on the tube 16 level with the weld to be checked so as to place the probe 11 in contact with the weld bead and so that the elements 110 of the probe cover the width of said weld bead 20. To do this, the inspecting device 10 may include a mark indicating the center of the detecting zone of the probes 11 so that this mark may be aligned with the center of the weld bead.

Once the device 10 has been positioned, the position of at least one probe 11 is acquired in order to define the initial position of the latter. The value of the signal representative of the initial position of the angle sensor 14 will for example be able to be stored in a memory zone 503 of the processing unit 50.

In certain embodiments of the device 10 according to the invention, the sensor 14 will possibly have a set initial position. The probes 11 will therefore be brought to a particular position corresponding to the origin of said angular sensor 14. In order to make it easier to locate the origin of the angle sensor 14, the means 13 may possess a locking notch.

The probes are then rotated using the means 13 and data acquired and these data recorded simultaneously at regular intervals as the probes 11 move. The collected data correspond to the signal representative of the angular position of at least one probe 11 relative to the initial position of the sensor 14 and of the signal representative of the echoes captured by the elements 110 of the probes 11 at this angular position.

According to one embodiment, the values of the measured signals are stored in a memory zone of the processing unit in order to be able to be processed for example by the computational module 502 of the processing unit 50. According to one variant embodiment, the display will be updated as the probes 11 rotate.

The invention claimed is:

1. A portable device for inspecting a weld bead of a small-diameter metal tubes, comprising:
    at least one clamp formed from two jaws, each jaw including a circularly arcuate void defining, once the clamp has been closed, a substantially circular slot with two lateral portions, suitable for receiving a tube the weld of which is to be inspected;
    at least two multielement ultrasound probes mounted so as to be movable relative to said inspecting device and that are mounted so as to be able to rotate relative to an axis passing through the center of the two lateral portions of the substantially circular slot of the clamp, said probes being configured to transmit an ultrasound beam and to deliver as output electrical signals proportional to a plurality of echoes they receive;
    an actuator configured to drive each of the ultrasound probes to rotate so as to make a complete turn around an entire circumference of the weld to be inspected; and
    an angular sensor configured to deliver as output a signal representative of an angular position of at least one of the probes relative to an initial position;
    each probe comprising several adjacent probe elements arranged in a row, in a number such that they cover at least the width of the weld to be inspected, each probe element being electronically controlled individually, the elements of said ultrasound probes being respectively aligned along two axes that are not symmetric about an axis passing through the center of the two lateral portions of the substantially circular slot of a clamp.

2. The device as claimed in claim 1, wherein the adjacent probe elements are configured to emit ultrasound beams that are oriented at an angle different from 90° to an axis passing through the center of the two lateral portions of the substantially circular slot of the clamp.

3. The device as claimed in claim 1, wherein the actuator configured to drive the ultrasound probes to rotate is a manual actuator.

4. The device as claimed in claim 1, wherein the actuator configured to drive the ultrasound probes to rotate is a motorized actuator.

5. A system for inspecting a weld bead of metal tubes, comprising the device for inspecting a weld bead of metal tubes according to claim 1, a processing unit and a viewing unit, said processing unit being configured to emit signals in the direction of each ultrasound probe of said weld inspecting device so as to control each probe element of said probes and to receive signals proportional to a plurality of echoes received by each probe element of said probes, the viewing unit being configured to represent, on said viewing unit, the signals received from the probes after processing in the form of images as a function of the angular position of at least one probe.

6. The system as claimed in claim 5, wherein the processing unit is programmed to transmit, to each element of the multielement probes, switching signals so as to sequentially power a group of adjacent probe elements in order to linearly scan a width of the weld bead to be inspected.

7. The system as claimed in claim 5, wherein the processing unit is configured to transmit, to each element of the probes, control signals respecting a delay law so as to electronically deviate the ultrasound beam emitted by said probes.

8. The system as claimed in claim 5, wherein the processing unit is configured to transmit, to each probe element of the multielement probes, a signal proportional to the intensity of the ultrasound beam to be emitted by said probes.

9. A method for inspecting a weld bead of metal tubes employing the weld inspecting system as claimed in claim 5, comprising:
    a step of coating probes with coupling gel;
    a step of positioning the inspecting device on the tube, level with the weld to be inspected so as to align the probes with said weld;
    a step of acquiring, to a memory zone of the processing unit, the signal representative of the current angular position of at least one probe;
    a step of rotating the probes around the weld bead to be inspected and, at regular intervals, simultaneously measuring and recording, to a memory zone of the processing unit, the signal representative of the angular position of at least one probe and the signal representative of a plurality of echoes captured by the elements of the probes; and a step of displaying, on the viewing unit, images representative of the signals received by the probe elements of the probes as a function of the angular position of said probes.

* * * * *